US007153327B1

(12) United States Patent
Metzger

(10) Patent No.: US 7,153,327 B1
(45) Date of Patent: Dec. 26, 2006

(54) METHOD AND APPARATUS FOR MECHANICALLY RECONSTRUCTING LIGAMENTS IN A KNEE PROSTHESIS

(75) Inventor: Robert Metzger, Walkarusa, IN (US)

(73) Assignee: Biomet, Inc., Warsaw, IN (US)

( * ) Notice: Subject to any disclaimer, the term of this patent is extended or adjusted under 35 U.S.C. 154(b) by 52 days.

(21) Appl. No.: 10/082,514

(22) Filed: Feb. 25, 2002

(51) Int. Cl.
*A61F 2/38* (2006.01)
*A61F 2/08* (2006.01)

(52) U.S. Cl. .............................. 623/20.29; 623/20.22; 623/13.12

(58) Field of Classification Search ............ 623/13.12, 623/20.14, 20.21, 20.22, 20.24–20.26, 20.28, 623/20.29, 20.33, 23.41, 20 FOR
See application file for complete search history.

(56) References Cited

U.S. PATENT DOCUMENTS

| 4,597,766 | A | | 7/1986 | Hilal et al. | |
|---|---|---|---|---|---|
| 4,770,663 | A | | 9/1988 | Hanslik et al. | |
| 5,002,574 | A | * | 3/1991 | May et al. | 623/13.13 |
| 5,067,962 | A | | 11/1991 | Campbell et al. | |
| 5,282,867 | A | | 2/1994 | Mikhail | |
| 5,534,033 | A | * | 7/1996 | Simpson | 623/13.14 |
| 6,004,351 | A | | 12/1999 | Tomita et al. | |
| 6,004,352 | A | * | 12/1999 | Buni | 623/20.33 |
| 6,203,576 | B1 | | 3/2001 | Afriat et al. | |
| 6,592,622 | B1 | * | 7/2003 | Ferguson | 623/13.14 |

FOREIGN PATENT DOCUMENTS

| FR | 2634373 | | 7/1988 |
|---|---|---|---|
| FR | 2663837 | | 1/1992 |
| FR | 2 734 709 A1 | * | 12/1996 |
| GB | 2129306 A | | 5/1984 |
| JP | 10-127672 A | * | 5/1998 |
| RU | 2 051 647 C1 | * | 1/1996 |
| RU | 2 076 667 C1 | * | 4/1997 |

\* cited by examiner

*Primary Examiner*—David H. Willse
(74) *Attorney, Agent, or Firm*—Harness, Dickey & Pierce, P.L.C.

(57) ABSTRACT

The invention relates to a knee joint prosthesis for replacing the articulating knee portion of a femur and a tibia. The knee joint prosthesis includes a femoral component, a tibial component, a bearing member, a guide post and a mechanically reconstructed ligament. The femoral component includes a first femoral bearing surface and a second femoral bearing surface. The tibial component includes a tibial bearing surface. The bearing member includes a first bearing surface which is operable to articulate with the first femoral bearing surface, a second bearing surface which is operable to articulate with the second femoral bearing surface and a third bearing surface which is operable to articulate with the tibial bearing surface. The guide post extends from the tibial component. The mechanically reconstructed ligament is coupled to both the tibial component and the femoral component to prevent the knee joints from dislocating and guiding the femoral component along a desired path during extension and flexion.

4 Claims, 5 Drawing Sheets

METHOD AND APPARATUS FOR MECHANICALLY RECONSTRUCTING LIGAMENTS IN A KNEE PROSTHESIS

FIELD OF THE INVENTION

This invention relates generally to a knee joint prosthesis which replaces the articulating knee portion of the femur and tibia, and more particularly, to a knee joint prosthesis having a mechanically reconstructed ligament.

BACKGROUND OF THE INVENTION

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint.

Motion of a natural knee is kinematically complex. During a relatively broad range of flexion and extension, the articular or bearing surfaces of a natural knee experience axial rotation, adduction and abduction, translation in the sagittal plane (rollback and sliding), and translation in the coronal plane. Knee joint prostheses, in combination with ligaments and muscles, attempt to duplicate this natural knee motion, as well as absorb and control forces generated during the range of flexion.

One type of knee joint prosthesis that is commonly known is a fixed bearing knee. In a fixed bearing knee, a femoral component is attached to a resected portion of the femur and a tibial component is attached to a resected portion of the tibia. The fixed bearing knee also includes a bearing member having a integral stem that is fixed to the tibial component. The bearing member allows articulation of the femoral component along a bearing surface formed on the bearing member. As the joint moves into flexion, the bearing surfaces and the post cause the femoral component to rollback and slide in the sagittal plane. The movement in the sagittal plane increases the mechanical advantage, and thus the efficiency of the quadriceps. However, fixed bearing knees sometimes exhibit drawbacks. First, increased contact stresses may be created between the femoral component and the bearing member. The stresses are caused by relatively limited conformance of the femoral component to the bearing surface during flexion of the joint. Second, fixed bearing knees may become dislocated if the bearing member "jumps" off of the post. Lastly, the post may reduce the length of the trochlea groove which may lead to clunking of the patella.

Another type of knee joint prosthesis that has proven effective especially with respect to rollback is a floating bearing knee. In a floating bearing knee, a femoral component is attached to a resected portion of the femur and a tibial component is attached to a resected portion of the tibia with a floating bearing positioned therebetween. The floating bearing includes bearing surfaces that articulate with both the tibial component and the femoral component. As the joint moves into flexion, the ligaments and soft tissues of the knee, as well as a fixed post help to translate the floating bearing posteriorly causing rollback of the femur and leading to proper positioning of the patella, increasing the extension moment arm and increasing quadricep efficiency. However, floating bearing knees may also experience various drawbacks. Just like fixed bearing knees, floating bearing knees may experience dislocations of the femoral component to the tibial component and clunking of the patella during flexion of the joint.

Knee joint replacements are also sometimes unable to utilize all of the natural ligaments and the soft tissue supporting the knee joint. Depending on the degree of damage or deterioration of the ligaments, it may be necessary for a knee joint to eliminate one or more of motions of the knee joint in order to provide adequate stability. The use of a mechanical replacement ligament with a knee joint prosthesis is therefore desirable.

What is needed then is a knee joint prosthesis that has a mechanical ligament. This in turn, will provide femoral rollback relative to the tibial component by means of the mechanical ligament, provide a mechanically reconstructed ligament to constrain undesired translation of the knee joint, increase the overall reliability of the knee joint prosthesis, and prevent anterior movement of the bearing. It is, therefore, an object of the present invention to provide a fixed or floating bearing knee joint prosthesis having a mechanically reconstructed ligament that achieves the above-identified advantages.

SUMMARY OF THE INVENTION

In accordance with the teachings of the present invention, a knee joint prosthesis having a mechanically reconstructed ligament for use in replacing the articulating knee portion of a femur and a tibia is disclosed.

In one preferred embodiment, a knee joint prosthesis for replacing the articulating knee portion of a femur and a tibia includes a femoral component, a tibial component, a bearing member, a guide post and a linkage mechanism. The femoral component includes a first femoral bearing surface and a second femoral bearing surface. The tibial component includes a tibial bearing surface. The bearing member includes a first bearing surface which is operable to articulate with the first femoral bearing surface, a second bearing surface which is operable to articulate with the second femoral bearing surface and a third bearing surface which is operable to articulate with the tibial bearing surface. The guide post extends from the tibial component. The linkage mechanism attaches the femoral component to the tibial component for controlling movement of the femoral component relative to the tibial component.

The use of the present invention provides a knee joint prosthesis with a mechanically reconstructed ligament. The knee joint prosthesis provides desired motion between its components from full extension to full flexion. As a result, the aforementioned disadvantages associated with the currently available knee joint prostheses have been substantially reduced or eliminated.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments concerning a knee joint replacement with a mechanically reconstructed ligament and a tibial post are merely exemplary and are not intended to limit the invention or its application or uses.

Figure 1:
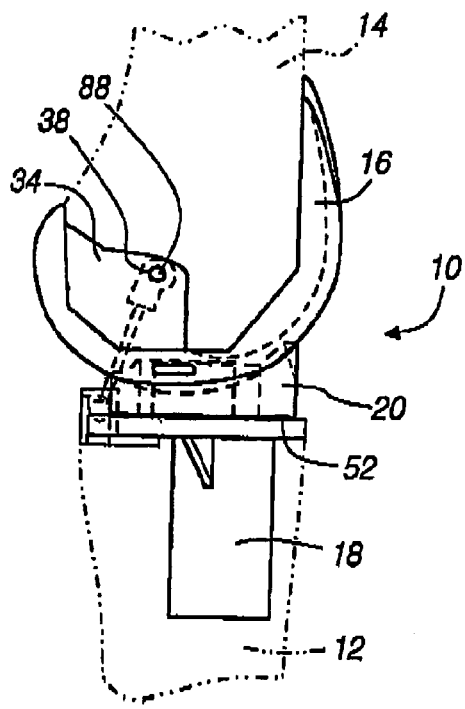
FIG. 1 is a perspective view of a posterior stabilized (PS) knee joint prosthesis according to the teachings of a first embodiment of the present invention.
Figure 2:
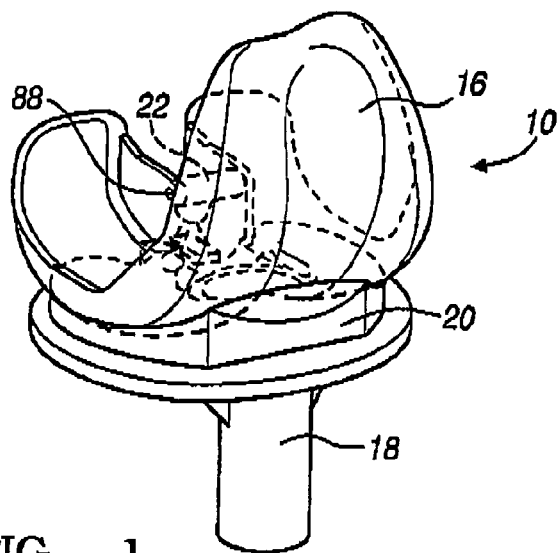
FIG. 2 is an exploded perspective view of a tibial component and bearing element of the knee joint prosthesis of FIG. 1.
Figure 3:
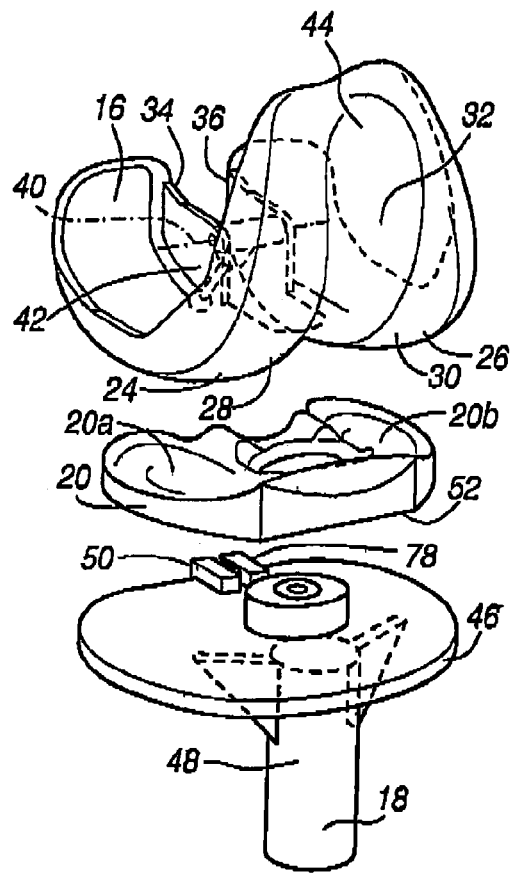
FIG. 3 is a sagittal elevational view of the knee joint prosthesis shown in FIG. 1 with a tibia and a femur of the natural knee shown in phantom.
Figure 4:
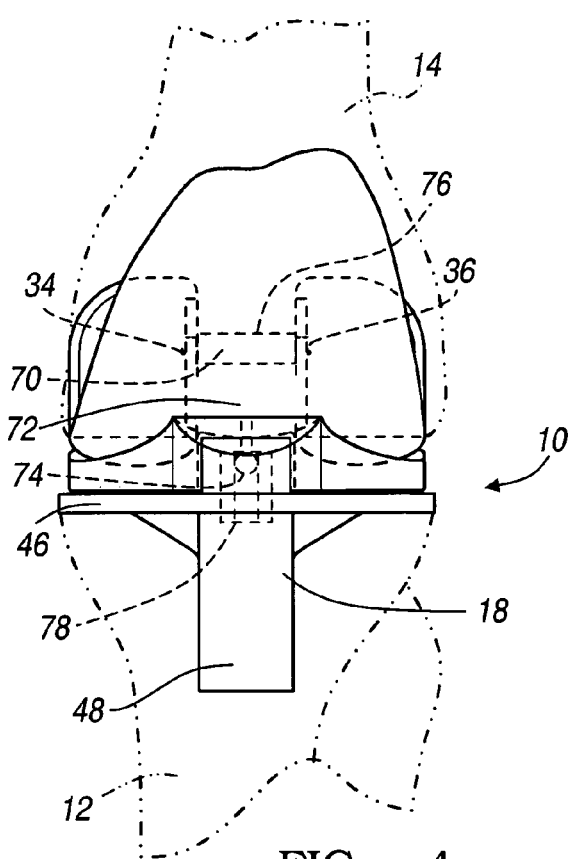
FIG. 4 is a coronal elevational view of the knee joint prosthesis shown in FIG. 1 with the tibia and the femur of the natural knee shown in phantom.
Figure 5:
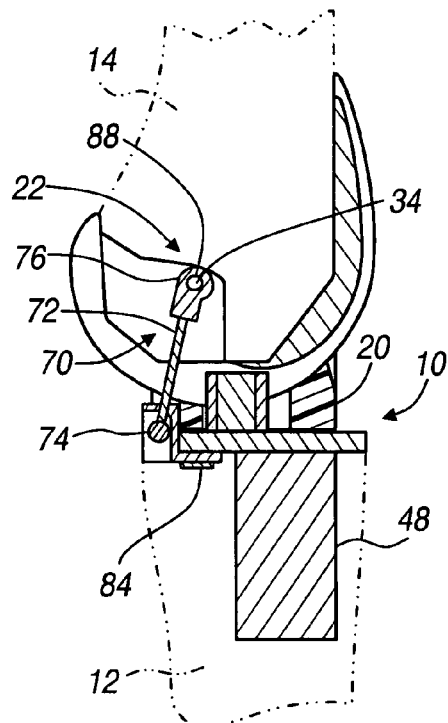
FIG. 5 is a sagittal sectional view of the knee joint prosthesis of FIG. 1.

Referring to FIGS. 1–8e, a knee joint prosthesis 10 is shown in accordance with the teachings of a first embodiment of the present invention. The knee joint prosthesis 10 is generally designed to be used when the posterior cruciate ligament (PCL) is resected. However, it is appreciated that the present invention may be utilized in knee replacements where other ligaments such as the anterior cruciate ligament (ACL) or other soft tissues that support the knee joint are resected. The knee joint 10 is shown in FIGS. 3–5 as being secured to the tibia 12 and the femur 14 of a surgically resected left knee joint, with the tibia 12 and the femur 14 shown in phantom, and with the understanding that a suitable right knee may be similarly constructed. The knee joint prosthesis 10 includes a femoral component 16, a tibial component 18, a floating bearing 20 and a linkage mechanism 22 coupling the femoral component 16 to the tibial component 18 and acting as the PCL replacement.

The femoral component 16 is adapted to be secured to a distal end of the femur 14 and includes a first condylar portion 24 and a second condylar portion 26 that provide a first bearing surface 28 and a second bearing surface 30, respectively. The first and second condylar portions 24 and 26 are interconnected by an intercondylar portion 32. The intercondylar portion 32 includes a medial rib 34 and a lateral rib 36 that are substantially planar and parallel to one another. Both the medial rib 34 and the lateral rib 36 include a bore 38 formed therethrough forming a rotation axis 40 substantially defined in the lateral and medial directions to connect the femoral component 16 to the linkage mechanism 22. The medial rib 34 and the lateral rib 36 substantially define an intercondylar recess 42 between the first and second condylar portions 24 and 26. Should further stability be required with respect to the femoral component 16, a femoral stem as is known in the art may be adapted for use with the present invention.

The femoral component 16 further includes an arcuate patellar portion 44 which is disposed on the anterior portion of the femoral component 16. The patellar portion 44 is shaped to allow anatomical tracking of a natural or prosthetic patella. The patella prostheses which are compatible with the present invention may be of varying shape, such as round or domed shaped and may be constructed from polyethylene, polyethylene with metal backing or other suitable materials. The femoral component 16 is preferably formed as a unitary structure and preferably cast of a biocompatible high strength alloy such as cobalt-chromium-molybdenum alloy or other suitable material. All surfaces which do not contact the femur 14 are preferably highly polished to provide smooth articulating bearing surfaces.

The tibial component 18 is adapted to be secured to the proximal end of the tibia 12 after the tibia 12 has been resected in a manner known in the art. The tibial component 18 includes a substantially planar platform-like tibial tray 46, an inferiorly extending tibial stem 48 and a linkage connection 50. The tibial stem 48 is adapted to be received in a corresponding opening made by the surgeon in the longitudinally center of the tibia 12. The linkage connection 50 is adapted to engage a portion of the linkage mechanism 22. The tibial tray 46 and stem 48 are preferably manufactured of cobalt-chromium-molybdenum alloy or other suitable biocompatible material. The top of the tibial tray 46 is highly polished to provide a substantially smooth tibial bearing surface 54.

The floating bearing 20 is located between the femoral component 16 and the tibial component 18. The floating bearing 20 has a substantially planar inferior bearing surface 52 which slidably moves relative to the highly polished tibial bearing surface 54, further discussed herein. The floating bearing 20 further includes a first bearing surface 20a and a second bearing surface 20b. The first bearing surface 20a and the second bearing surface 20b articulate with the first bearing surface 28 of the condyle 24 and the second bearing surface of the condyle 26 of the femoral component 16, respectively. Positioned between the first and second bearing surfaces 20a and 20b is a circular, or other appropriate shapes as discussed opening 60 that is slidably positioned around a guide post 62. The opening 60 is defined by a substantially perpendicular peripheral sidewall 64 which is operable to engage the guide post 62. The floating bearing 20 is preferably formed from a surgical grade, low friction, low wearing plastic, such as UHMWPE or other suitable material.

The center guide post 62 includes a substantially oval shaped outer peripheral sidewall 66 or any other appropriately shaped sidewall, such as those disclosed in U.S. Pat. No. 6,165,223 and commonly assigned U.S. patent application Ser. No. 09/659,448 entitled "Floating Bearing Knee Joint Prosthesis With A Fixed Tibial Post", which are hereby incorporated by reference. The guide post 62 is preferably formed to be removably attached to the tibial component 18 by a threaded fastener 68 or any other suitable means. Additionally, the guide post 62 may be formed integral with the tibial component 18. The center guide post 62 is preferably formed of cobalt-chromium-molybdenum alloy or other suitable biocompatible material. The peripheral sidewall 66 of the guide post 62 is highly polished to provide a substantially smooth surface to articulate with the generally, and exemplary, rectangular opening 60. It is also contemplated that the guide post 62 be constructed of an alloy having a polymeric material defining the peripheral sidewall 66 to provide a substantially smooth surface to articulate with the floating bearing 20. Alternatively, the guide post 62 may be removed from the knee joint prosthesis 10 to provide a different constraint on the floating bearing 20 and the femoral component 16.

The linkage mechanism 22 operatively connects the femoral component 16 to the tibial component 18 to allow proper kinematic movement between the femoral component 16 and the tibial component 18 at the floating bearing 20. The linkage mechanism 22 is coupled to the femoral component 16 by bores 38 formed in the lateral and medial ribs 34 and 36. The linkage mechanism 22 is coupled to the tibial component 18 at the linkage connection 50. As stated, the linkage mechanism 22 serves to replace a resected PCL, thus the linkage mechanism 22 must function in a similar manner to a natural PCL whereby, posterior translation of the tibia 12 in either flexion or extension is controlled. However, it is appreciated that the linkage mechanism 22 may be coupled to the femoral component 16 and the tibial component 18 in various locations to simulate the natural function of many different ligaments.

In a first embodiment shown in FIGS. 1–10, the linkage mechanism 22 is comprised of a T-shaped linkage 70 coupled to the femoral component 16 and to the tibial component 18. The T-shaped linkage 70 is comprised of a bar 72 having a ball 74 on a first end and a perpendicularly oriented shaft 76 on the other end. The T-shaped linkage 70 is shown to be formed of a bar 72 having a braided steel cable coated with a polymer to allow the linkage 70 to be flexible. However, it is contemplated that the T-shaped linkage 70 may be formed of various materials having varying mechanical properties or combinations of materials to optimize the performance of the knee joint prosthesis 10. For example, the T-shaped linkage 70 may be rigid, flexible, resilient and made from materials such as nylon, surgical steel or UHMWPE to provide the desired characteristics.

The ball end 74 of the linkage 70 is coupled to the tibial component 18 by a captured slot 78 that permits rotation and translation of the T-shaped linkage 70 with respect to the tibial component 18. The captured slot 78 includes a superior extending aperture 80 corresponding to the size and shape of the ball end 74 of the T-shaped linkage 70 and a stop 82 preventing translation of the ball end 74 past the captured slot 78 while permitting relative rotation. The captured slot 78 is preferably fastened to the tibial component 18 by a threaded fastener 68 or other suitable device or formed integral therewith.

The shaft 76 end of the linkage 70 is coupled to the femoral component 16 at the bores 38 formed in the lateral and medial rib 34 and 36. The shaft 76 end of the linkage 70 includes a first and second outwardly extending spring biased pins 88 that engage the bores 38 in the lateral and medial ribs 34 and 36, respectively. The coupling of the shaft 76 end of the linkage 70 to the bores 38 of the femoral component 16 permits the femoral component 16 to pivot around a fixed axis substantially similar to normal kinematic movement of a knee joint.

As the knee joint 10 is moved from extension to flexion, a natural PCL restrains the tibia 12 to prevent posterior movement of the tibia 12 relative to the femur 14 and promotes rollback of the femur 14 in the posterior direction to allow for proper positioning of the patella. Likewise, the linkage mechanism 22 of the present invention also accomplishes the same function. When the knee joint 10 is flexed, the ball end of the T-shaped linkage 70 travels along the captured slot 78. If the tibia 12 (or tibial component 18) translates in the posterior direction to a predetermined maximum amount, the mechanical linkage engages the tibial component 18 and the femoral component 16 to prevent further translation of the tibia 12 in the posterior direction. When increased flexion occurs, the shaft 76 end of the T-shaped linkage 70 pivots around the rotation axis 40 defined by the bores 38. The eccentric location of the rotation axis 40 causes the femur 14 (femoral component 16) to translate posteriorly as additional flexion occurs. The floating bearing 20 also translates posteriorly or a forced rollback of the bearing occurs as the bearing surfaces engage the bearing surfaces of the first and the second condyles.

Figure 6:
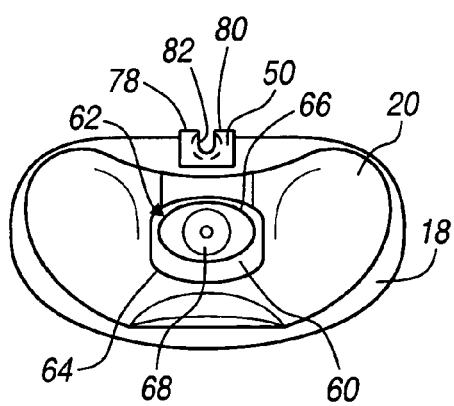
FIG. 6 is a top view of the assembled tibial component and bearing member of FIG. 1.
Figure 7:
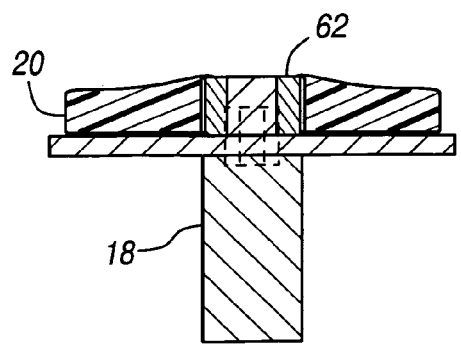
FIG. 7 is a coronal sectional view of the tibial component and bearing member of the knee joint prosthesis of FIG. 1.

Turning to FIGS. 6 and 7, tibial component 18 and the floating bearing 20 are shown with the posterior stabilized guide post 62. In this regard, the guide post 62 is positioned just posteriorly the opening 60 defined by the sidewall 64. However, it is appreciated that the present invention may be utilized with anterior stabilized, fully constrained, primary, cruciate retaining and many other types of knee replacements presently known.

Figure 8A:
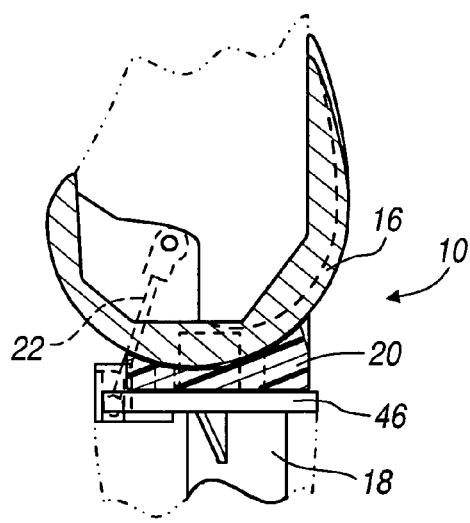
FIGS. 8a–8e are partial sagittal sectional views of the knee joint prosthesis shown in FIG. 1 illustrating five different positions of the femoral component with respect to the tibial component during a range of flexion from full extension to full flexion.
Figure 8B:
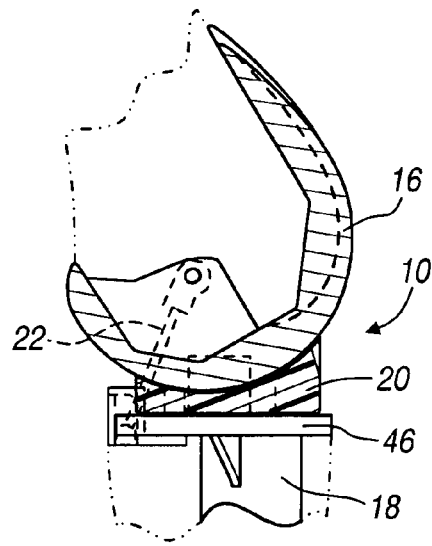
Figure 8C:
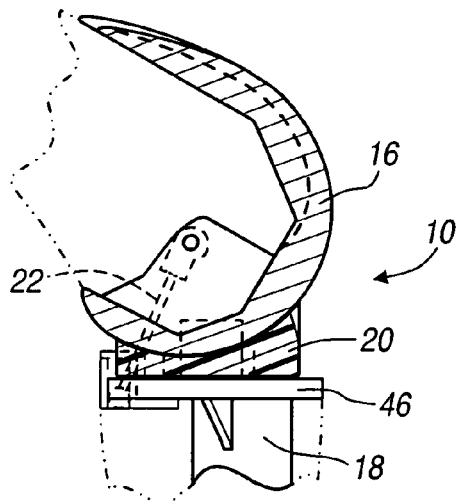
Figure 8D:
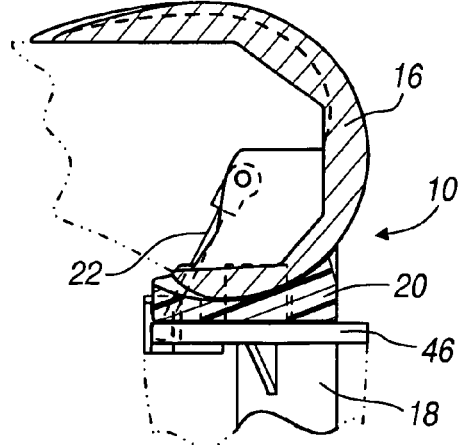
Figure 8E:
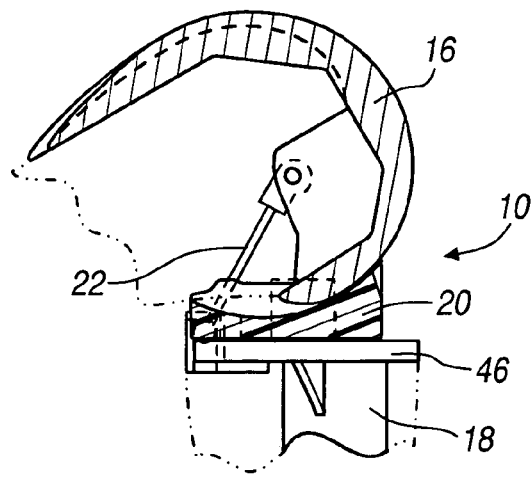
Figure 9:
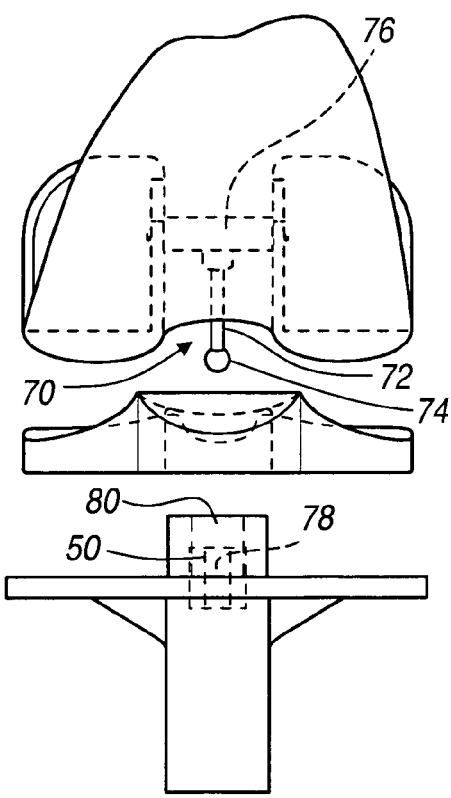
FIG. 9 is an exploded coronal elevational view of a knee joint prosthesis according to the teachings of a second embodiment of the present invention.
Figure 10:
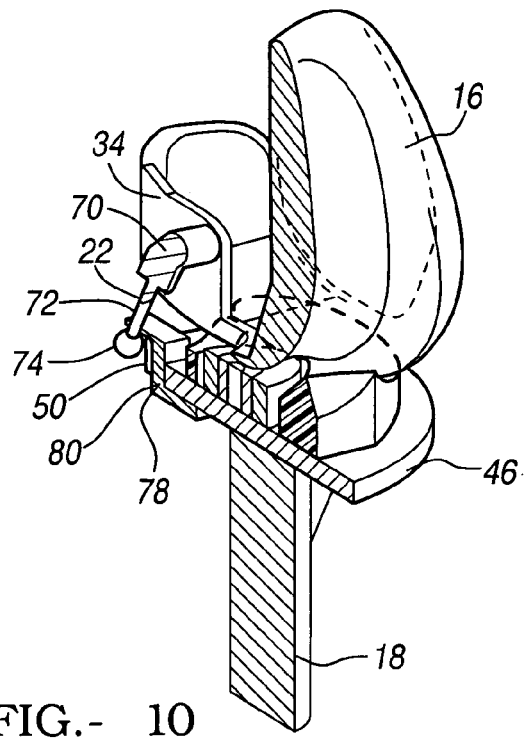
FIG. 10 is a sagittal sectional perspective view of the knee joint prosthesis of FIG. 9.

Turning to FIGS. 8a–8e, partial sagittal sectional views of the knee joint prosthesis 10 illustrating the movement of the femoral component 16, the floating bearing 20 and the linkage mechanism 22 relative to the tibial component 18 are shown from full extension in FIG. 8a to full flexion in FIG. 8e. In FIG. 8a, the knee joint prosthesis 10, both anteriorly and posteriorly, is inherently stable at full extension when the patient is standing. In this position, the first and second femoral bearing surfaces are rested within the first and second bearing surfaces 28 and 30 of the floating bearing 20, respectively. If the knee joint prosthesis 10 would undergo a large hyperextension or forward rollback (approximately 10 degrees), the linkage mechanism 22 would engage the femoral component 16 and the tibial component 18. This engagement will further avoid posterior dislocation of the femoral component 16 relative to the tibial component 18.

The femoral component 16 with respect to the tibial component 18 and the floating bearing 20 is generally most unrestricted between full extension, as illustrated in FIG. 8a and the point of flexion where the linkage mechanism 22 begins to engage the femoral component 16 and the tibial component 18 generally, as illustrated in FIG. 8b. This engagement generally occurs between about 20 degrees to 45 degrees of flexion. Within this range between 0 degrees to about 20 degrees to 45 degrees, the femoral component 16 is permitted to translate in the sagittal plane along with the floating bearing 20 relative to the tibial component 18. However, it is appreciated that the linkage mechanism would ideally engage the femoral component 16 and the tibial component 18 during the entire range of motion of the knee joint. For example, a flexible linkage mechanism may be used to ensure constant engagement of the linkage mechanism.

In particular, the femoral component 16 will remain substantially congruently positioned relative to the floating bearing 20 to provide a full articulating contact surface during this range of flexion. In other words, the femoral component 16 and the floating bearing 20 are both able to move anteriorly and posteriorly relatively freely with respect to the tibial component 18, via the bearing surfaces between the floating bearing 20 and the tibial tray 46. However, it should be further understood that the exact amount of translation in the sagittal plane permitted by the knee joint prosthesis 10 will of course, vary depending on the forces imparted by local soft tissues, muscles, tendons, ligaments, as well as forces transmitted from the tibia 12 and femur 14. These forces will, of course, vary from patient to patient, from activity to activity, as well as from implantation to implantation.

When flexion exceeds approximately 20 degrees to 45 degrees, rollback of the floating bearing 20 posteriorly relative to the tibial tray 46 occurs. Rollback of the floating bearing 20 is caused when the linkage mechanism 22 engages both the tibial component 18 and the femoral component 16 to prevent relative anterior-posterior translation therebetween. While this forced rollback of the floating bearing 20 is occurring, the bearing surfaces of the first and second condyles 24 and 26 are fully nestingly received within the bearing surfaces of the floating bearing 20. This forced rollback of the floating bearing 20 creates the desired femoral rollback of an anatomical knee joint. As flexion continues from about 60 degrees shown in FIG. 8c to about 110 degrees shown in FIG. 8e, a forced rollback of the floating bearing 20 relative to the tibial tray 46 continues to occur, while a surface contact area between the first and second condyles 24 and 26 and the floating bearing 20 increases with flexion of the joint, via cooperating surfaces.

As can be observed from FIGS. 8a–8e, the forced rollback enables the surface contact area between the femoral component 16 and the floating bearing to be increased during flexion of the joint 20. This full surface contact is achieved because rollback is occurring between the floating bearing 20 and the tibial component 18, via a sliding of the floating bearing 20 posteriorly atop the tibial tray 46. It should also be noted that since the linkage 70 is positioned centrally and perpendicular to the coronal plane, rotational freedom of the femoral component 16 relative to the tibial component 18 is maintained.

Figure 11:
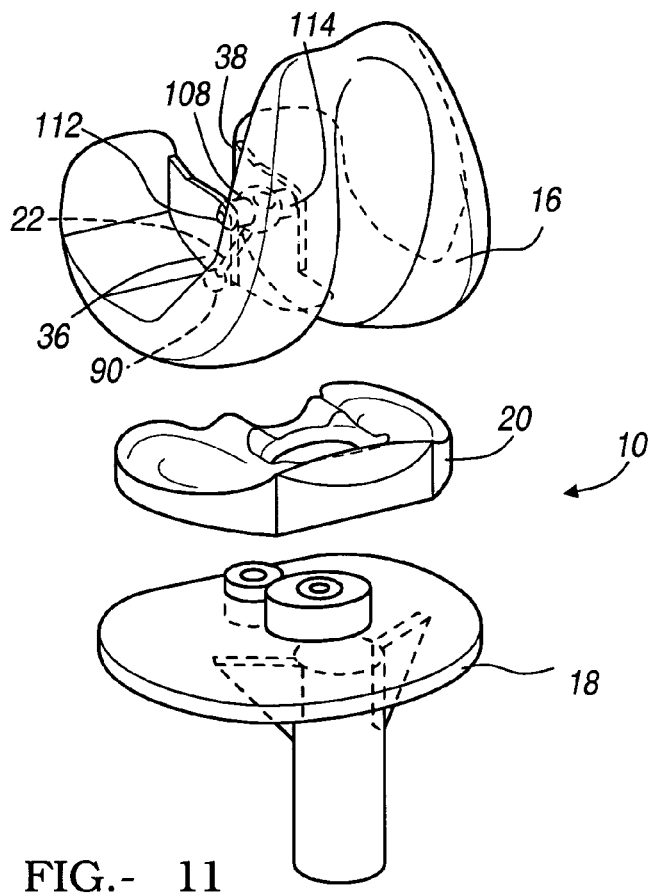
FIG. 11 is a exploded perspective view of the knee joint prosthesis of FIG. 9.
Figure 12:
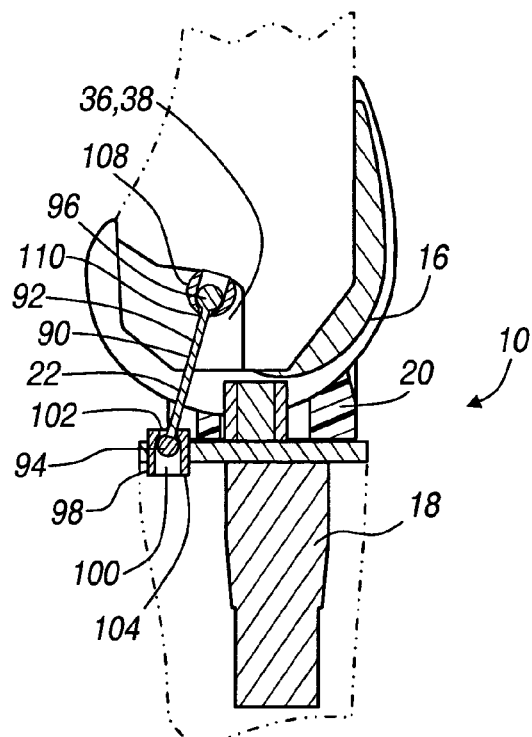
FIG. 12 is a partial sagittal sectional view of the knee joint prosthesis of FIG. 9.

As shown in FIGS. 11–12, a second embodiment of a linkage mechanism 90 for the prosthetic knee joint 10 having the floating bearing 20 is shown comprised of a bar 92 coupled to the femoral component 16 and to the tibial component 18. The bar 92 includes a first ball 94 attached to a first end and a second ball 96 attached to the second end. The bar 92 is shown to be formed of a rigid biocompatible metal such as cobalt-chromium-molybdenum alloy having suitable mechanical properties. However, it is contemplated that the bar 92 may be formed of various materials having varying mechanical properties or combinations of materials to optimize the performance of the knee joint prosthesis 10. For example, the bar 92 may be rigid, flexible, resilient and made from materials such as nylon, surgical steel or UHM-WPE to provide the desired characteristics.

The first ball 94 end of the bar 92 is coupled to the tibial component 18 by a captured bore 98 that permits rotation and translation of the linkage mechanism 90 with respect to the tibial component 18. The captured bore 98 includes a superior extending aperture 100 corresponding to the size and shape of the ball end 94 of the bar 92 and a stop 102 preventing translation of the ball end 94 past the end of the captured bore 98 while permitting relative rotation. The captured bore 98 is preferably fastened to the tibial component 18 by a threaded fastener 104 or other suitable device.

The second ball 96 end of the bar 92 is coupled to the femoral component 16 by a trunnion 108 having a captured bore 110 therein and rotatably coupled to the lateral and medial ribs 34 and 36. The trunnion 108 includes a first and second screws 112 and 114 that engage the bores 38 in the lateral and medial ribs 34 and 36, respectively. The coupling of the ball end 96 of the linkage to the bores 38 of the femoral component 16 permits the femoral component 16 to pivot around a fixed axis substantially similar to normal kinematic movement of a knee joint, as shown in FIGS. 8a–8c.

The methodology of replacing the articulating knee joint 10 of the present invention includes a plurality of steps. First, the distal end of the femur is resected to form a new end substantially conforming to the femoral component 16. Second, bone cement is applied to either the femoral component 16 or the femur 12 and the end of the femur and the femoral component are positioned to allow the bone cement to adhere. Third, the proximal end of the tibia is resected and an axial bore is drilled along the center of the tibia. The size of the hole is substantially similar to the size of the tibial post 48. Fourth, the tibial component 18 is coupled to the tibia by a press fit of the tibial post 48 into the bore drilled in the tibia. Next, the floating bearing 20 is installed over the guide post 62 to replicate the meniscus of the knee. Next, the tibial component 18 and the femoral component 16 are aligned so that all of the bearing surfaces are allowed to properly articulate with each other. Lastly, the linkage mechanism 22 is installed to couple the femoral component 16 to the tibial component 18.

To install the linkage mechanism 22 according to the first embodiment the ball end 74 of the linkage 70 is guided into engagement with the captured slot 78 located on the tibial component. Next, the other end of the linkage 70 is coupled to the femoral component 16. The spring biased pins 88 located on the shaft are depressed to allow the shaft 76 to be positioned in the bore 38 located in the lateral and medial ribs 34 and 36. When the shaft is in position, the spring biased pins 88 will engage the bores 38 of the femoral component 16 and provide a coupling to the femoral component 16.

To install the linkage mechanism 90 according to the second embodiment, the bar 92 is guided into engagement with the captured bore 98 and the bore 110 of the trunnion 108. The ball 94 is installed on the end of the bar 92 to secure the first end of the linkage 90 to the tibial component. Next, the trunnion 108 is coupled to the medial and lateral ribs of the femur with threaded fasteners. The ball end 96 is installed on the end of the bar 92 to prevent the end of the bar from moving through the bore 110. Thus, the linkage couples the femoral component 16 and the tibial component 18 together.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of replacing the articulating knee portion of a femur and a tibia comprising:
   resecting an end portion of the tibia;
   resecting an end portion of the femur;
   attaching a tibial prosthetic component corresponding to the resected end portion of the tibia, the tibial prosthetic component having a bearing surface;
   attaching a femoral prosthetic component corresponding to the resected end portion of the femur, the femoral prosthetic component having a bearing surface;
   installing a bearing member between the tibial prosthetic component and the femoral prosthetic component, the bearing member having a first surface operable to articulate with the femoral bearing surface and a second bearing surface operable to articulate with the tibial bearing surface; and connecting the tibial prosthetic component to the femoral prosthetic component with a linkage, the linkage operable to allow the femoral prosthetic component to translate in the posterior direction and rotate during flexion of the joint;

wherein connecting the tibial prosthetic component to the femoral prosthetic component with the linkage further includes the step of inserting a first end of the linkage into a guide located in the tibial prosthetic component, inserting the second end of the linkage into a guide located in the femoral prosthetic component, installing a first stop on the first end of the linkage to prevent the first end of the linkage from passing through the guide on the tibial prosthetic component and installing a second stop on the second end of the linkage to prevent the second end of the linkage from passing through the guide on the femoral prosthetic component.

2. A method of replacing the articulating knee portion of a femur and a tibia comprising:

resecting an end portion of the tibia;

resecting an end portion of the femur;

attaching a tibial prosthetic component corresponding to the resected end portion of the tibia, the tibial prosthetic component having a bearing surface;

attaching a femoral prosthetic component corresponding to the resected end portion of the femur, the femoral prosthetic component having a bearing surface;

installing a bearing member between the tibial prosthetic component and the femoral prosthetic component, the bearing member having a first surface operable to articulate with the femoral bearing surface and a second bearing surface operable to articulate with the tibial bearing surface; and connecting the tibial prosthetic component to the femoral prosthetic component with a linkage, the linkage operable to allow the femoral prosthetic component to translate in the posterior direction and rotate during flexion of the joint;

wherein connecting the tibial prosthetic component to the femoral prosthetic component with the linkage further includes inserting the linkage into a captured slot in the tibial component, translating the linkage until a first end portion of the linkage engages the captured slot, connecting a second end portion of the linkage to the femoral prosthetic component.

3. A method of replacing the articulating knee portion of a femur and a tibia comprising:

resecting an end portion of the tibia;

resecting an end portion of the femur;

attaching a tibial prosthetic component corresponding to the resected end portion of the tibia, the tibial prosthetic component having a bearing surface;

attaching a femoral prosthetic component corresponding to the resected end portion of the femur, the femoral prosthetic component having a bearing surface;

installing a bearing member between the tibial prosthetic component and the femoral prosthetic component;

allowing the bearing member, having a first surface operable to articulate with the femoral bearing surface and a second bearing surface operable to articulate with the tibial bearing surface, to articulate with both of the tibial prosthetic component and the femoral prosthetic component;

connecting the tibial prosthetic component to the femoral prosthetic component with a linkage; and allowing the femoral prosthetic component to translate in the posterior direction and rotate during flexion relative to the tibial prosthetic component of the joint because of the linkage;

wherein connecting the tibial prosthetic component to the femoral prosthetic component with the linkage includes:

inserting the linkage into a captured slot in the tibial component;

translating the linkage until a first end portion of the linkage engages the captured slot; and connecting a second end portion of the linkage to the femoral prosthetic component.

4. The method of claim 3, wherein connecting the tibial prosthetic component to the femoral prosthetic component with the linkage includes:

connecting a first end of the linkage to a posterior portion of the tibial prosthetic component; and connecting a second end of the linkage to a interior portion of the femoral prosthetic component.

* * * * *